United States Patent [19]

Pugh et al.

[11] Patent Number: 4,954,334

[45] Date of Patent: Sep. 4, 1990

[54] FOOT POWDER COMPOSITION

[76] Inventors: Monroe S. Pugh; Robert L. Pugh, both of Rte. 1, Box 48, Mouth of Wilson, Va. 24363

[21] Appl. No.: 296,483

[22] Filed: Jan. 12, 1989

Related U.S. Application Data

[63] Continuation-in-part of Ser. No. 2,560, Jan. 12, 1987, abandoned.

[51] Int. Cl.$^5$ .................................................. A61K 7/38
[52] U.S. Cl. ........................................ 424/68; 424/65
[58] Field of Search .................. 424/659, 682, 698, 68, 424/65, 76.1

[56] References Cited

U.S. PATENT DOCUMENTS

| | | | |
|---|---|---|---|
| 52,032 | 1/1866 | Clayton | 424/68 |
| 161,944 | 4/1875 | Gahn | 424/659 X |
| 1,371,822 | 3/1921 | Tate | 424/68 |
| 1,885,292 | 11/1932 | Ritter | 424/659 |
| 2,073,634 | 3/1937 | Hodnefield et al. | 424/659 X |
| 2,210,013 | 8/1940 | Teller | 424/68 |
| 3,180,827 | 4/1965 | Martinek et al. | 424/659 X |
| 4,117,115 | 9/1978 | Hutchins | 424/659 |

FOREIGN PATENT DOCUMENTS

| | | | |
|---|---|---|---|
| 44-8571 | 4/1969 | Japan | 424/659 |
| 8501770 | 9/1985 | Netherlands | 424/659 |

*Primary Examiner*—Thurman K. Page
*Attorney, Agent, or Firm*—Norman B. Rainer

[57] ABSTRACT

A perspirant suppressant powder composition specially adapted to be applied to a person's feet is comprised of boric acid and aluminum ammonium sulfate. The composition produces long lasting effects following initial application.

4 Claims, No Drawings

4,954,334

FOOT POWDER COMPOSITION

RELATED APPLICATIONS

This application is a continuation-in-part of U.S. Pat. application Ser. No. 002,560 filed Jan. 12, 1987 by the same inventors and now abandoned.

BACKGROUND OF THE INVENTION

This invention concerns a powder composition to be applied to the skin of a person's feet as a perspiration suppressant.

Many compositions have heretofore been proposed for application to the feet for the purposes of preventing perspiration or odors, or for cooling or heating effects, or to provide still other beneficial effects. The compositions are generally in powder form and are applied by entering the composition into the foot portions of hose such as socks and stockings. Ingredients of such compositions have generally included inorganic compounds of aluminum, zinc and zirconium having an astringent effect upon the skin; substances which prevent irritation of the skin; and anti-microbial compounds. The astringent compounds function by closing the pores of the skin that encase sweat glands, and thereby minimize the production of perspiration.

Anti-perspirant compositions of the prior art are generally effective only while in contact with the skin, and do not condition the skin so as to suppress perspiration after removal of the composition.

Furthermore, some prior compositions are not suitable for treatment of feet and some may produce allergic reactions, cumulative long term skin sensitivities, or staining of the socks.

It is accordingly an object of this invention to provide a perspiration suppressant composition of long duration effectiveness.

It is another object of this invention to provide a composition as in the foregoing object which, upon application to feet, conditions the skin so as to suppress perspiration even after removal of the composition.

It is a further object of the present invention to provide a composition of the aforesaid nature of low cost and which does not produce allergic skin reactions.

These objects and other objects and advantages of the invention will be apparent from the following description.

SUMMARY OF THE INVENTION

The above and other beneficial objects and advantages are accomplished in accordance with the present invention by a powder composition consisting essentially of 40 to 60 parts by weight of boric acid powder and 40 to 60 parts by weight of aluminum ammonium sulfate powder.

BRIEF DESCRIPTION OF THE PREFERRED EMBODIMENT

The composition of the invention is prepared by the mixing of appropriate weight amounts of the two ingredients, each being in the form of a dry powder having a particle size small enough to pass through a 100 mesh sieve screen. Optional ingredients in quantities of less than about one percent may be included within the composition, said ingredients being, for example, anti-microbials, fragrances, anti-caking agents and moisture absorbents.

In use, amounts of the composition ranging between about 15 and 45 grams are placed into each sock. The composition thereby works its way into complete contact with the skin of the foot, including the areas between the toes, and areas around the heel. The composition is preferably placed into the socks in the morning, thereby permitting contact with the feet for at least eight hours until the socks and shoes are removed at night.

When the suppressant composition is initially utilized, the rate of perspiration will actually increase for the first two to three days before tapering off and stopping completely. The skin of the feet thus treated with the composition is toughened, and will remain free of perspiration and attendant odor without further use of the powder for about four to six months.

The aforesaid manner of treatment of feet with the composition of this invention has been found not to produce adverse effect such as allergic reactions, pain or discomfort. The socks utilized for treatment are not stained by the composition, and the composition is completely removable from the socks by ordinary laundering techniques.

The effectiveness of the composition of the present invention is attributable to the highly critical selection of the two primary ingredients and the ratio of their combinations. The aluminum ammonium sulfate (alum) acting in conjunction with boric acid serves to bind the outer epidermis layer to the underlying dermis or true skin while concurrently toughening the fibers of the skin to make it nearly water tight. The alum functions as a powerful astringent that draws together the fibers of the skin. The boric acid opens the pores of the skin, allowing penetration of the dermis by the alum while preventing the alum from harming or drying out the skin. In view of such effect, perspiration is actually increased with initial application of the composition of this invention.

Although aluminum salts have been generally and specifically disclosed for use in anti-perspirant compositions, the use of aluminum ammonium sulfate in particular in such compositions appears to be novel, and its combination with a substantially equal amount of boric acid is particularly novel and unobvious. Although prior references allude to the use of "alum" in anti-perspirant compositions, the term alum is a broad designation for hydrated metal sulfates containing two cation moieties. A preferred form of aluminum ammonium sulfate useful in the practice of this invention is "ammonium alum" having the empirical formula:

$$Al_2(SO_4)_3 \cdot (NH_4)_2 SO_4 \cdot 24 H_2O$$

A two percent solution of said compound in water has a pH of 3.47. Other aluminum ammonium sulfates may be prepared by the addition of various amounts of ammonium hydroxide to an aqueous solution of aluminum sulfate $Al_2(SO_4)_3$ followed by drying at low temperature and powdering. However, to be acceptable for use in the composition of this invention, a two percent aqueous solution of the compound should have a pH between 3.4 and 3.5. A two percent aqueous solution of boric acid has a pH of 3.59.

When placed in water, a two percent concentration of the composition of this invention will produce a pH between 3.5 and 3.6. Because of the presence of a weak acid such as boric acid, a weakly basic cation such as $NH_4+$, and amphoteric $Al+++$ cations, the composition is highly buffered; and such buffered effect is in part responsible for the effectiveness of the composition. The data of the following table verify the buffered nature of the composition. In said data, two percent solutions of composition of this invention of varying constitution are found to produce the same pH.

| Composition | pH |
| --- | --- |
| Aluminum Ammonium Sulfate 40% Boric Acid 60% | 3.53 |
| Aluminum Ammonium Sulfate 50% Boric Acid 50% | 3.53 |
| Aluminum Ammonium Sulfate 60% Boric Acid 40% | 3.53 |

The following example further illustrates certain specific features of the present invention.

EXAMPLE

A composition of the present invention consisting of 50% by weight boric acid powder and 50% by weight of aluminum ammonium sulfate was employed in treating the feet of 60 human subjects, 12 female and 48 male, ranging in age from 14 to 58 years.

The subjects were grouped as follows: Category 1—twelve female and 36 male subjects with moderate perspiration with foot odor. Category 2—three male subjects with heavy perspiration. Category 3—seven male subjects with moderate perspiration with foot odor and "athletes foot". Category 4—two male subjects with heavy perspiration and "athletes foot".

The composition was employed by placing one heaping tablespoon (about 19 grams) in the foot portion of each sock to be worn by the subject, working the sock back and forth to uniformly coat the inside of the sock. The composition was further worked between the toes of the subject. The thus treated sock was worn for eight hours per day.

In Category 1 subjects, the composition was applied for five consecutive days for 24 test subjects and for six consecutive days for 24 test subjects. The rate of perspiration was found to increase for the first two to three days for about 80% of the subjects tested before the perspiration began tapering off and stopping. There was no significant difference in applying the composition for six days than for five days if the perspiration was stopped within five days. The test subjects whose perspiration was stopped in about four days experienced between four and five months without any perspiration or odor. Those test subjects whose perspiration stopped in about five days experienced between five and six months of no odor or perspiration. This established that, the longer the perspiration can be initially sustained, the greater will be the duration of the subsequent period of non-perspiration.

In the Category 2 subjects, two had foot odor while one had no foot odor. The skin was cracked under the toes of one test subject. The work shoe life for the three subjects was about four to five months. The composition of the invention was applied for six consecutive days. It took much longer for the perspiration to stop for these test subjects than for those tested in Category 1. In less than two weeks after the composition was applied, the perspiration had stopped and in less than three weeks the skin was completely healed. These test subjects experienced between seven and eight and one-half months of no perspiration or odor. The test subjects' shoes were still in good condition after a year and four months.

In the Category 3 subjects, the composition was applied for five consecutive days. The results were about the same for these test subjects as they were for the test subjects in Category 1; the only difference being that a few days after the perspiration had stopped, there was no sign of athletes foot until the perspiration returned.

In the Category 4 subjects, the skin was cracked between the toes of both test subjects. The composition was applied for six consecutive days. In less than two weeks after the composition of the invention was applied, the perspiration stopped. In less than three weeks, the skin was completely healed and there was no sign of athletes foot. These test subjects experienced about seven months before any perspiration or athletes foot returned.

None of the subjects tested experienced any discomfort, irritation, or allergic reaction of any kind—even those with broken skin. The tests further establish that the composition is safe and effective for controlling foot perspiration, odor, and athletes foot.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described our invention, what is claimed is:

1. A composition for suppressing perspiration of the feet consisting essentially of boric acid powder and aluminum ammonium sulfate powder, said powders each being present to the extent of 40% to 60% by weight of the composition, said aluminum ammonium sulfate being characterized in that its two percent aqueous solutions will have a pH between 3.4 and 3.5, a two percent aqueous solution of the composition having a pH between 3.5 and 3.6.

2. A process for suppressing perspiration of the feet comprising applying to the feet an effective amount of a composition consisting essentially of boric acid powder and aluminum ammonium sulfate powder, each powder being present to the extent of 40% to 60% by weight of the composition.

3. A process for suppressing perspiration of a person's feet comprising the procedure of placing an effective amount of between about 15 and 45 grams the composition of claim 1 in each sock of a pair, said socks being then worn by the person for about eight hours, and repeating said procedure for a period of at least 5 days, during which period perspiration of the feet is increased, then discontinuing said procedure, whereupon the feet remain free of perspiration for at least months.

4. The composition of claim 1 wherein a two percent aqueous solution has a pH of about 3.53.

* * * * *